United States Patent [19]

Hare

[11] Patent Number: 5,661,222
[45] Date of Patent: Aug. 26, 1997

[54] POLYVINYLSILOXANE IMPRESSION MATERIAL

[75] Inventor: Robert V. Hare, Georgetown, Del.

[73] Assignee: Dentsply Research & Development Corp., Milford, Del.

[21] Appl. No.: 490,690

[22] Filed: Apr. 13, 1995

[51] Int. Cl.$^6$ .................................................. A61K 6/10
[52] U.S. Cl. ........................... 525/478; 528/15; 528/31; 528/32; 528/39; 523/109; 264/16; 106/38.22; 106/35; 433/214; 524/493; 524/588
[58] Field of Search ....................... 525/478; 528/31, 528/32, 15, 39; 523/109; 264/16; 106/38.22, 35; 433/214; 524/493, 588

[56] References Cited

U.S. PATENT DOCUMENTS

| | | | |
|---|---|---|---|
| 2,676,182 | 4/1954 | Daudt et al. | 260/448.2 |
| 2,857,356 | 10/1958 | Goodwin | 260/42 |
| 3,527,659 | 9/1970 | Keil | 117/145 |
| 3,950,300 | 4/1976 | Hittmair et al. | 260/37 |
| 3,957,683 | 5/1976 | Hittmaier et al. | 252/428 |
| 4,035,453 | 7/1977 | Hittmair et al. | 525/478 |
| 4,222,983 | 9/1980 | August et al. | 260/220 |
| 4,248,750 | 2/1981 | Murakami et al. | 260/29.1 |
| 4,276,252 | 6/1981 | Kreis et al. | 264/222 |
| 4,288,345 | 9/1981 | Ashby et al. | 252/431 R |
| 4,359,565 | 11/1982 | Puppe et al. | 528/15 |
| 4,387,240 | 6/1983 | Berg | 556/440 |
| 4,424,328 | 1/1984 | Ellis | 526/279 |
| 4,535,141 | 8/1985 | Kroupa | 528/15 |
| 4,575,545 | 3/1986 | Nakos et al. | 526/242 |
| 4,593,084 | 6/1986 | Chandra et al. | 528/15 |
| 4,600,731 | 7/1986 | Louis et al. | 523/109 |
| 4,657,959 | 4/1987 | Bryan et al. | 524/266 |
| 4,687,870 | 8/1987 | Cavezzan | 556/136 |
| 4,719,273 | 1/1988 | Seyforth et al. | 528/15 |
| 4,722,968 | 2/1988 | Shimizu et al. | 524/862 |
| 4,741,966 | 5/1988 | Cavezzan | 428/447 |
| 4,752,633 | 6/1988 | Aasen et al. | 524/266 |
| 4,772,515 | 9/1988 | Hara et al. | 428/447 |
| 4,776,704 | 10/1988 | Kopunek et al. | 366/184 |
| 4,782,101 | 11/1988 | Waller et al. | 523/120 |
| 4,806,575 | 2/1989 | Waller et al. | 523/120 |
| 4,806,592 | 2/1989 | Saruyama | 524/860 |
| 4,836,853 | 6/1989 | Gribi | 106/35 |
| 4,845,164 | 7/1989 | Gulek | 528/15 |
| 4,849,491 | 7/1989 | Ogawa et al. | 528/15 |
| 4,882,398 | 11/1989 | Mbah | 525/478 |
| 4,906,446 | 3/1990 | Engelbrecht et al. | 423/335 |
| 4,916,169 | 4/1990 | Boardman et al. | 522/27 |
| 4,957,667 | 9/1990 | Hamer | 264/16 |
| 4,965,295 | 10/1990 | Schwabe et al. | 523/109 |
| 5,004,792 | 4/1991 | Maxson | 528/15 |
| 5,064,891 | 11/1991 | Fujiki et al. | 524/264 |
| 5,085,811 | 2/1992 | Hamer | 264/16 |
| 5,145,933 | 9/1992 | Grisoni et al. | 528/15 |
| 5,169,919 | 12/1992 | Terae et al. | 528/15 |
| 5,239,035 | 8/1993 | Maxson | 528/15 |
| 5,288,830 | 2/1994 | Itoh et al. | 528/15 |
| 5,306,797 | 4/1994 | Ikeno | 528/15 |
| 5,331,075 | 7/1994 | Sumpler et al. | 528/15 |
| 5,371,162 | 12/1994 | Konings et al. | 528/15 |
| 5,403,885 | 4/1995 | Voight et al. | 524/731 |

FOREIGN PATENT DOCUMENTS

| | | |
|---|---|---|
| 2030435 | 5/1991 | Canada . |
| 0268347 | 5/1988 | European Pat. Off. . |
| 0522341 | 6/1992 | European Pat. Off. . |
| 4129613 | 3/1993 | Germany . |
| 93/17654 | 9/1993 | WIPO . |

Primary Examiner—Margaret W. Glass
Attorney, Agent, or Firm—James B. Bieber; Douglas J. Hura

[57] ABSTRACT

Improved two component polymerizable polyorganosiloxane compositions are described, particularly for use in making dental impressions, having improved tear strength and wettability. Improved tear strength results from inclusion of a quadri-functional polysiloxane having a vinyl content of 0.16 to 0.24 m-mole/g. Working time is maintained by including sufficient amounts of a retarder composition that delays onset of the vinyl polymerization. Wettability is improved by including a surfactant resulting in a surface contact angle with water at three minutes of less than 50°. The surfactant chosen has an HLB of 8–11, such that the wetting contact angle is achieved within less than two minutes and remains wetting throughout the working time of the impression taking, substantially improving the impression making process.

26 Claims, 1 Drawing Sheet

POLYVINYLSILOXANE IMPRESSION MATERIAL

BACKGROUND OF THE INVENTION

This invention is directed to improvements in room temperature polymerizable polyorganosiloxanes having good dimensional stability upon curing or hardening. More particularly, this invention is directed to improvements in compositions that are generally of the type comprising two components, one component comprising organopolysiloxanes having vinyl groups, capable of undergoing addition reactions with organopolysiloxanes having silicone-bonded hydrogen atoms. The second component comprises a catalyst capable of promoting the addition of hydrogen atoms bonded to silicone atoms across the vinyl groups.

A major field for the use of certain of these room temperature curable polyorganosiloxane compositions is dentistry. Such materials are typically employed as impression materials for securing an analog representation of oral hard and soft tissue to support subsequent elaboration of crowns, bridges, dentures, an other oral prostheses. For dental use, extraordinary fidelity of structural reproduction is required in order to ensure good fidelity of oral prosthetic fit and the like. In this regard, changes in the dimensions of the impression material during curing are to be avoided. Moreover, the surface of the reproductions or oral prosthetics and the like must be exceptionally free from irregularities, blemishes, pits, and other imperfections. This is so because castings and prostheses derived from such impressions must have good surface qualities and be free from pits and irregularities in order to have proper fit, to achieve good adhesion, and to avoid irritation of sensitive mouth structures. These polyorganosiloxanes will also be useful in other fields where detailed reproductions are important such as in the science of metrology, laboratory processing of SEM and even jewelry fabrication and the like.

In employing polyorganosiloxanes as dental impression materials, a number of difficulties have arisen. First of all, tear strength tends to be low. It is necessary, in effectively taking an impression, to be able to easily remove the impression, from the dentition without tearing, particularly at thin marginal areas, to preserve fine detail. In the past, fillers of various types have been added to improve tear strength. Such additions may result in some improvement, on the order of about 10%, but such improvements have proved inadequate.

Paradiso in WO 93/17654 describes improving tear strength by incorporating multi-functional, including quadri-functional, polysiloxane components into the impression material, to add increased cross-linking to the resulting cured impression material matrix, particularly along the length of the linear vinyl end-stopped polysiloxane principal component. The Paradiso composition comprises SiOH groups capped off with $Me_3Si$ units that form pendants from the molecule. These pendants provide only mechanical or physical interlinking between the linear polysiloxane chains. This solution is deficient, being non-chemical and low in cross-linking density.

Voigt et al in EP 0 522 341 A1 describes very short processing times of 35–45 seconds for forming dentition bite registration devices, utilizing a "QM" resin as a means of speeding and increasing cross-linking. These resins comprise as Q, the quadri-functional $SiO_{4/2}$ and as M, building blocks such as monofunctional units $R_3SiO_{1/2}$ wherein R is vinyl, methyl, ethyl or phenyl, or similar tri or bi-functional units. Voigt notes that an elastomer with small elastic deformation having a higher tenacity and hardness results. However, such material lacks flexibility, having a low strain value, and is unsuitable for impression taking. The increased cross-linking rate of the QM resin also results in very limited processing times that are unsatisfactory.

The other major, well-known difficulties with polyorganosiloxane impression materials are caused by its inherent hydrophobic character. Such characteristics make reproduction of hard and soft oral tissue difficult since the oral cavity environment is wet and often contaminated with saliva or blood. The hydrophobicity of the impression material can result in loss of surface detail often at critical surfaces of the dentition.

A number of improvements of polyorganosiloxane impression materials focus upon adding a surfactant component to the dental impression material in order to reduce the hydrophobic nature of the polysiloxanes and make the composition more hydrophilic. Thus, Bryan et al in U.S. Pat. No. 4,657,959 describes adding an ethoxylated nonionic surface active agent containing siloxane or perfluoroalkyl solubilizing groups to achieve a three minute water contact angle below about 65°. While surfactants including hydrocarbyl groups, for rendering the surfactant soluble or dispersible in silicone prepolymer, are mentioned, including ethyleneoxy groups, the results achieved appeared to be less than optimal.

In sum, polyorganosiloxane impression materials still need improvement in tear strength and wettability in order to provide improved use of these compositions for taking impressions of oral hard and soft tissues such that adequate working time, tear strength and wettability are provided.

SUMMARY OF THE INVENTION

The new polyvinylsiloxane impression materials are useful in low and high viscosity impression materials to record hard and soft tissues in the mouth. The new impression material is a two component, platinum-catalyzed, vinylpolysiloxane material. The two component polymerizable organosiloxane composition, one component including a catalyst for polymerization, for making a dental impression, comprises:

(a) a QM resin, containing vinyl groups;

(b) a linear vinyl terminated polydimethylsiloxane fluid, forming with said QM resin a dispersion having a vinyl content of about 0.16 to 0.24 m-mole/g;

(c) an organohydrogen polysiloxane for cross-linking said vinyl groups;

(d) an organoplatinum catalyst complex for accelerating polymerization of said components;

(e) an emulsifying plasticizer for said catalyst complex;

(f) a retarder component in sufficient amount for temporarily delaying the onset of said polymerization;

(g) a filler; and (h) a surfactant that imparts wettability to said composition, wherein said composition surface contact angle with water is less than 50° after three minutes.

Preferably, the dispersion of (a) and (b) has a viscosity of about 5,000–60,000 cps. The dispersion of (a) and (b) may comprise a plurality of dispersion components having desired viscosities and QM resin contents. Preferably the QM resin-containing dispersions comprise a first dispersion component having a viscosity of about 5,000–7,000 cps; and a second dispersion component having a viscosity of about 45,000–60,000 cps, said QM resin comprising about 20–25 weight % of each dispersion.

A preferred QM resin comprises a polyorganosiloxane comprising units of $SiO_{4/2}$ and units of $R^1R^2{}_2 SiO_{1/2}$ wherein $R^1$ is unsaturated, preferably vinyl and $R^2$ is alkyl, aryl, etc., such as methyl, ethyl, phenyl, etc. More preferably, the QM resin comprises the formula:

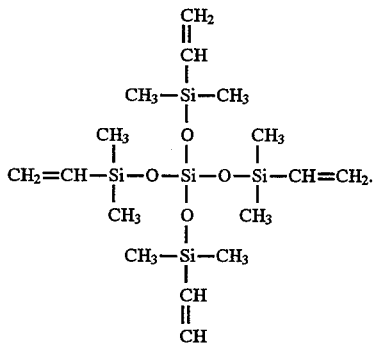

The retarder component of the composition is a low molecular weight, vinyl functional fluid that is a linear or cyclic polysiloxane in an amount of at least about 0.030 weight percent of said composition. Preferably, the retarder component comprises: a fluid 1,3-divinyl, dimethyldisiloxane, in an amount of about 0.030 to 0.10 weight percent of said composition.

The composition includes an emulsifying plasticizer that imparts desired handling and flow properties to the catalyst complex, to match those of the second component, wherein a suitable composition for taking a dental impression may conveniently be formed. Preferably, the plasticizer comprises an alkylphthalate at about 0.5 to 2.0% by weight of said catalyst component and is, most preferably, octyl benzyl phthalate.

The filler component of the invention comprises about 15 to about 45 weight percent of said composition and preferably includes a filler mixture of about 20 to about 40 weight percent.

A key component of the composition of the invention is the surfactant for imparting wettability, preferably comprising an HLB of about 8–11 and a pH of about 6–8. A most preferred surfactant is a nonionic surfactant, nonylphenoxy poly (ethyleneoxy) ethanol having an HLB of about 10.8.

After polymerization, the compositions of the invention include a tear strength of 270–300 PSI (1.86–2.06 MPa) and a contact angle with water of less than 50° at three minutes.

DESCRIPTION OF THE PREFERRED EMBODIMENTS

Figure 1:
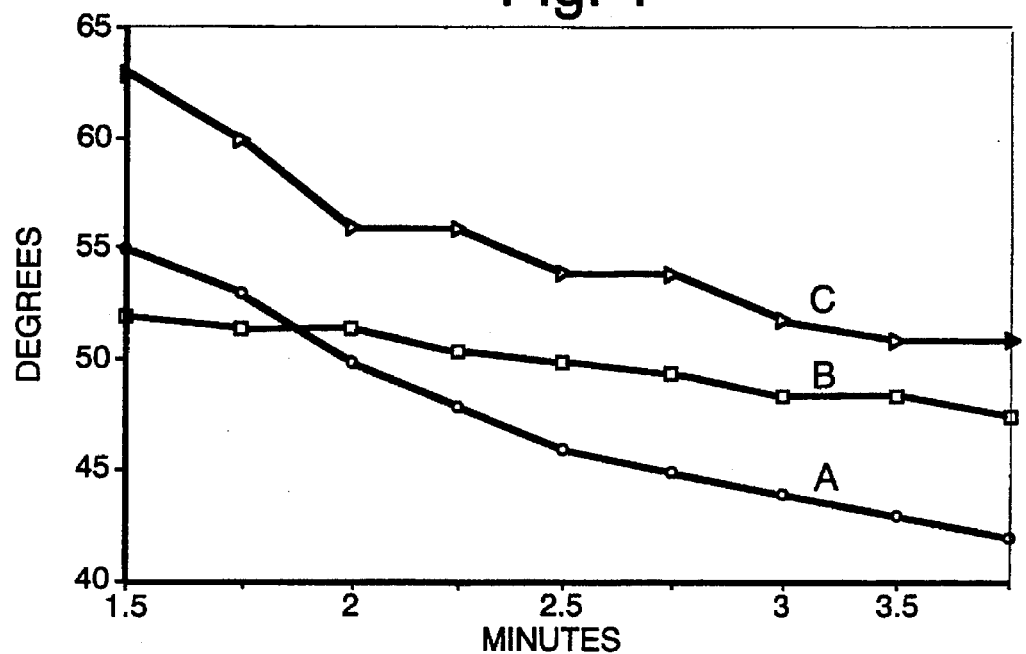
FIG. 1 is a graph showing Wetting Contact Angle, in degrees, as a function of Time, in minutes.

The two component, polymerizable polysiloxane compositions of the instant invention comprises, in general: an organopolysiloxane having at least about two vinyl groups per molecule, further including, dispersed therein, a quadri-functional vinyl polysiloxane resin; an organohydrogenpolysiloxane having at least about two hydrogen atoms bonded to at least two silicone atoms per molecule; a catalyst for accelerating the addition of the silicone atoms bonded to the hydrogen atoms to the polysiloxane vinyl groups, including an emulsifying plasticizer; a filler; a low molecular weight retarder composition for delaying onset of polymerization; and an emulsifying surfactant that imparts wettability to said impression material.

The composition of the invention is divided into two components. A first component, which is conveniently referred to as a "Base Paste", contains the vinylorganopolysiloxanes dispersion, the organo-hydrogen-polysiloxane, a portion of the filler and the surfactant. The second component of this two-part composition is referred to as a "Catalyst Paste" and comprises a second portion of the vinyl polysiloxanes, together with the catalyst for accelerating the addition reaction, the emulsifying plasticizer, a scavenging agent for hydrogen released during polymerization and usually, additional quantities of fillers and pigments.

A wide variety of organopolysiloxanes having at least about two vinyl groups per molecule are known for inclusion in the dental polysiloxane compositions of the invention to form the dispersion including a quadri-functional vinyl polysiloxane. Each of these materials may be included in greater or lesser degree in accordance with the practice of the instant invention. Preferred for use herein are linear vinyl terminated polydivinytsiloxanes preferably a divinyl polydimethylsiloxane. Such polymers are sold having varying average molecular weights with concomitant variations in viscosity. It is preferred that these materials be selected to have a viscosity appropriate for the conditions to be experienced by the resulting silicone material.

The dispersions of interest have a viscosity range of 5,000–60,000 cps. In practice, it is convenient to employ a blend of the dispersing polymers having differing viscosities and physical properties to provide compositions having a desired thixotropicity and viscosity.

The dispersions of interest are preferably formed in two viscosity ranges: (1) a first dispersion having a viscosity of about 5000–7000 cps; and (2) a second dispersion having a viscosity of about 45,000–65,000 cps. While it is convenient to provide polysiloxane oligomers for this purpose having methyl substituents, other substituents may also be included in the compositions in accordance with this invention. Thus, alkyl, aryl, halogen, and other substituents may be included in greater or lesser degree as part of the vinyl polysiloxanes which are useful. Those of ordinary skill in the art will be able to determine which polysiloxane materials are preferred for any particular utility from the foregoing considerations.

The quadri-functional polysiloxanes, designated and known in the art as QM resins, provide improved tear strength to the polymerized impression composition, by increasing its resulting polymerized crosslink density. As is known, the QM resin is made up of: quadri-functional $SiO_{4/2}$ units; and M units, such as $R^1R^2{}_2SiO_{1/2}$ wherein $R^1$ is unsaturated, preferably vinyl and $R^2$ is alkyl, aryl or the like, such as methyl, ethyl or phenyl. In a preferred composition $R^1$ is vinyl and both $R^2$ are methyl. A most preferred composition is represented by the formula:

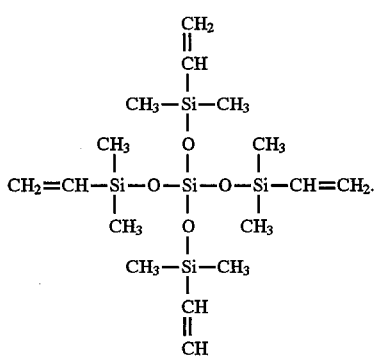

The QM resin provides a vinyl concentration in the dispersions with the vinyl-terminated polydivinylsiloxanes of at least about 0.16 m-mole/g. Preferably the vinyl concentration is 0.16–0.24 m-mole/g. The amount of QM resin is preferably about 20–25% by weight of the dispersion. Such dispersions are sold by Miles, Inc. of Pittsburg, Pa. Other QM resin formulations may be used, including those that are "neat" or dispersed in carriers other than the preferred fluid polydivinylsiloxane.

A key element of the invention is a retarder component that delays onset of polymerization of the QM resin/dispersion such that sufficient working times to employ the composition are provided. It functions, as it is consumed, to offset what would otherwise be a too rapid polymerization. The preferred retarder fluid in the preferred impression material of interest is 1,3 divinyldimethyldisiloxane at a sufficient concentration level to perform its retarding functions, which is in at least about 0.03 weight percent of the composition, preferably within a range of about 0.03 to 0.10 weight percent. This preferred amount is in contrast with the lower amounts of 0.0015–0.020 weight percent typically employed in PVS systems to stabilize compositions. Other suitable retarders are any low molecular weight, vinyl functional material that would be initially consumed in the polymerization, to delay hardening suitably and as desired, including linear and cyclic polysiloxanes.

The organohydrogen-polysiloxanes useful in the practice of the present inventions are well-known to those of ordinary skill in the art. It is required only that polysiloxanes having hydrogen atoms directly bonded to silicone atoms be employed, and that they have suitable viscosities and other physical properties. Substituents in the molecules such as alkyl (especially methyl), aryl, halogen, and others may be employed as well. It is necessary only that such substituents not interfere with the platinum-catalyzed addition reaction. It is preferred that molecules be employed having at least two silicone-bonded hydrogen atoms per molecule. Polymethylhydrogensiloxane is preferred, having viscosity range of about 35–45 cps.

The catalysts which are useful for catalyzing the reaction of the silicone atoms (bonded to hydrogen atoms) to the vinyl groups of the vinyl polysiloxane molecules are preferably based upon platinum. In this regard, it is preferred to employ a platinum compound such as chloroplatinic acid, preferably in admixture or complex with one or more vinyl materials, especially vinyl polysiloxanes. While such materials have been found to be preferred, other catalysts are also useful. Thus, platinum metal together with other noble metals including palladium, rhodium, and the like and their respective complexes and salts are also useful. In view of the toxicological acceptability of platinum, however, it is greatly to be preferred for dental use.

The compositions of the present invention also include a filler, preferably a mixture of hydrophobic fillers. A wide variety of inorganic, hydrophobic fillers may be employed such as silicas, aluminas, magnesias, titanias, inorganic salts, metallic oxides and glasses. It is preferred, however, that forms of silicone be employed, In accordance with the present invention, it has been found to be preferable to employ mixtures of silicones, including those derived form: crystalline silicone dioxide, such as pulverized quartz (4–6µ); amorphous silicone dioxides, such as a diatomaceous earth (4–7µ); and silanated fumed silica, such as Cab-o-Sil TS-530 (160–240 m²/g), manufactured by Cabot Corporation. The sizes and surface areas of the foregoing materials are controlled to control the viscosity and thixotropicity of the resulting compositions. Some or all of the foregoing hydrophobic fillers may be superficially treated with one or more silanating or "keying" agents, as known to those of ordinary skill in the art. Such silanating may be accomplished through use of known halogenated silanes or silazides. The fillers are present, preferably, in amounts of from about 15 to about 45 weight percent of the composition, forming an impression composition that is polymer rich and, thus, having improved flow properties. The fillers, more preferably, are about 35–40 weight percent of the composition. A preferred filler mixture includes 14–24 weight percent crystalline silicone dioxide, 3–6 weight percent amorphous silicone dioxide and 4–8 weight percent silanated fumed silicone dioxide. A most preferred filler is about 19% cristobalite at about 4–6µ particle diameter, about 4% diatomaceous earth at about 4–7µ particle diameter and about 6% silanated fumed silica at about 160–240 m²/g.

A chemical system may be employed to diminish the presence or degree of hydrogen outgassing which may be typically generated as a result of the vinyl polymerization. The composition thus may comprise a finely divided platinum metal that scavenges for and takes up such hydrogen. The Pt metal may be deposited upon a substantially insoluble salt having a surface area of between about 0.1 and 40m²/g. Suitable salts are barium sulphate, barium carbonate and calcium carbonate of suitable particle sizes. Other substrates include diatomaceous earth, activated alumna, activated carbon and others. The inorganic salts are especially preferred to lend improved stability to the resulting materials incorporating them. Dispersed upon the salts is about 0.2 to 2 parts per million of platinum metal, based upon the weight of the catalyst component. It has been found that employment of the platinum metal dispersed upon inorganic salt particles substantially eliminates or diminishes hydrogen outgassing during curing of dental silicones.

An important improvement of the invention is inclusion in the composition of a surfactant that imparts wettability to said composition, as indicated by a surface contact angle with water at three minutes of less than 50°. An unexpected result of the selection of surfactant provides a major clinical advantage in that the wetting contact angle of less than 50° is achieved in less than about two minutes, decreasing and remaining below 50° throughout the working time of the composition, in contrast with prior art polyvinylsiloxanes and surfactant formulations that require more time to wet out. This higher wetting rate of the composition of the invention is particularly advantageous during the impression taking process and is shown in the Drawings.

Figure 2:
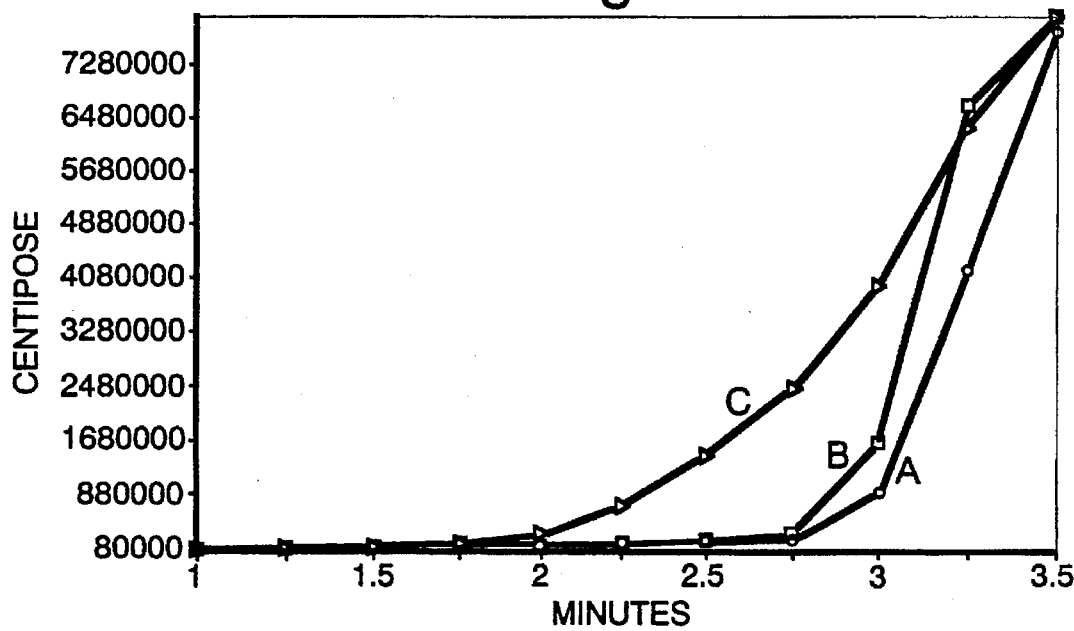
FIG. 2 is a graph showing Impression Material Viscosity as a function of Time, in minutes.

Referring to FIG. 1, the Wetting Contact Angle, in degrees, as a function of Time, in minutes, is shown for the polyvinyl siloxane composition of the invention, in comparison with prior art compositions. Curve A is the composition of the invention showing a wetting contact angle of about 50° at two minutes after mixing of the base and catalyst components. FIG. 1 demonstrates that good wettability is achieved early and improves at a fast rate over the about 3.5 minutes of useful working life of the impression taking material. Curves B and C are, respectively, polyether and conventional polyvinyl siloxane impression materials of the prior art. FIG. 2 shows Impression Material Viscosity as a function of Time for composition of the invention, Curve A, and the two prior art compositions B and C noted above. It shows the progression of the polymerization process from mixing and, in combination with FIG. 1, demonstrates that the improved wettability of the composition of the invention occurs during the critical working time for the impression material, an important advantages over other known systems.

The surfactant of the invention may be of cationic, anionic, amphoteric or nonionic type. A key criteria for selection is that the Hydrophobic Liphophilic Balance (HLB) value (described by Gower, "Handbook of Industrial Surfactants", 1993) must be in the range of 8–11. As is well-known, the higher the HLB the more hydrophobic is the substance. In addition, the pH of the surfactant must be in the 6–8 range to prevent side reactions that may be detrimental the polymerization of the impression. A preferred surfactant is nonionic, having an HLB value of 10.8 comprising nonylphenoxypoly(ethyleneoxy) ethanol, sold by Rhone-Poulenc of Cranbury, N.J. as Igepal CO-530. In comparison it is noted above with respect to Bryan et al, in U.S. Pat. No. '959 that Igepal CO-630, having an HLB of 13.0, differing in structure from CO-530 wherein the number of repeating units in CO-630 is 9 and those of CO-530 is 6, is not effective, demonstrating the criticality of the HLB limitation.

The composition of the invention includes plasticizers that beneficially alter the handling and flow properties of the impression material, particularly the catalyst component. A preferred emulsifying plasticizer is octyl benzyl phthalate. Other phthalates are useful.

The composition of the invention may include various pigments to achieve a preferred color. Such pigments are well known and include titanium dioxide as well as many others.

The two component compositions prepared in accordance with the instant invention are employed in the same way that conventional impression materials have been employed. Thus, appropriately equal portions of base paste and catalyst paste are mixed together thoroughly and applied to the oral dentition or other region for a period of time sufficient for the polymerizations or hardening of the composition. Once the composition has been substantially hardened, it is removed from the mouth or other surface and used for the elaboration of casts and the like from which representations of the casting surface are subsequently prepared.

As will be appreciated by those of ordinary skill in the art, it is important that dental silicone materials be capable of being stored for reasonably long periods of time and at reasonable storage temperature in order to maximize their commercial utility. Accordingly, it is necessary that such materials not suffer from decreased physical properties or substantial changes in working time or hardening time upon such storage. In this regard, accelerated storage tests employing high ambient temperatures are now capable of determining the shelf stability of such materials.

Certain embodiments of the present invention are described below. Numerous other compositions and formulations may be prepared within the spirit of the invention. The following examples are not to be construed as limiting and are offered by way of illustration.

Example 1

The two component composition of the invention is formulated in a Base Paste and Catalyst Paste components. Mixing of each component's ingredients is done in a double planetary mixer having a mixing pot heated with circulating water at 45° C.–50° C. and under 65 mm mercury vacuum.

BASE PASTE COMPONENT

In making the Base Paste, the mixing pot is first charged with all organohydrogen polysiloxane and incrementally thereafter, with QM dispersion and filler component, with mixing continuing until a uniform mixture is achieved. The finished Base Paste is discharged into a storage container.

CATALYST PASTE COMPONENT

The Catalyst Paste component is formulated and mixed under conditions and in equipment as described above. The platinum catalyst, 1,3 divinyldimethyldisiloxane, QM resin dispersions, fillers and pigments are added incrementally to the mixing pot and mixing carried out until a uniformly mixed mass is achieved. The compounded Catalyst Paste is then discharged into a storage container The composition of each component is indicated in the table below, wherein amounts are in weight percent of the component.

|  | BASE | CATALYST |
| --- | --- | --- |
| Organohydrogen Polysiloxane | 9.00 | 0.00 |
| (5000–7000 cps) QM resin dispersion | 19.62 | 23.95 |
| (45000–60000 cps) QM resin dispersion | 34.59 | 42.89 |
| Cristobalite | 19.01 | 19.06 |
| Diatomaceious earth | 6.53 | 6.41 |
| Cab-O-Sil TS-530 | 6.53 | 6.00 |
| Pigments Predispersed in Divinyl Polysiloxane | 0.65 | 0.25 |
| Titanium Oxide Pigment | 0.07 | 0.07 |
| Surfactant (Igepal CO-530) | 4.00 | 0.00 |
| Plasticizer | 0.00 | 0.50 |
| Platinum Catalyst | 0.00 | 0.64 |
| 1,3-Divinyldimethyidisiloxane | 0.00 | 0.07 |
| Finely divided Platinum metal on Calcium Carbonate | 0.00 | 0.16 |
|  | 100.00 | 100.00 |

Example 2

A two component composition of the invention is made by first making a Base Paste and then a Catalyst Paste as described in Example 1, having the composition indicated in the table below.

|  | BASE | CATALYST |
| --- | --- | --- |
| Organohydrogen Polysiloxane | 9.00 | 0.00 |
| (5000–7000 cps) QM resin dispersion | 20.18 | 31.71 |
| (45000–60000 cps) QM resin dispersion | 35.61 | 35.23 |
| Cristobalite | 19.74 | 20.67 |
| Diatomaceious earth | 4.30 | 4.28 |
| Cab-O-Sil TS-530 | 6.45 | 6.42 |
| Pigments Predispersed in Divinyl Polysiloxane | 0.65 | 0.25 |
| Titanium Oxide Pigment | 0.07 | 0.07 |
| Surfactant (Igepal CO-530) | 4.00 | 0.00 |
| Plasticizer | 0.00 | 0.50 |
| Platinum Catalyst | 0.00 | 0.64 |
| 1,3-Divinyldimethyidisiloxane | 0.00 | 0.07 |
| Finely divided Platinum metal on Calcium Carbonate | 0.00 | 0.16 |
|  | 100.00 | 100.00 |

Example 3

A two component composition of the invention is made by first making a Base Paste and then a Catalyst Paste as described in Example 1, having the composition indicated in the table below.

|  | BASE | CATALYST |
|---|---|---|
| Organohydrogen Polysiloxane | 10.00 | 0.00 |
| (5000–7000 cps) QM resin dispersion | 14.73 | 26.91 |
| (45000–60000 cps) QM resin dispersion | 43.80 | 43.80 |
| Cristobalite | 17.00 | 17.40 |
| Diatomaceious earth | 5.00 | 5.00 |
| Cab-O-Sil TS-530 | 5.00 | 5.00 |
| Pigments Predispersed in Divinyl Polysiloxane | 0.40 | 0.50 |
| Titanium Oxide Pigment | 0.07 | 0.07 |
| Surfactant (Igepal CO-530) | 4.00 | 0.00 |
| Plasticizer | 0.00 | 0.50 |
| Platinum Catalyst | 0.00 | 0.65 |
| 1,3-Divinyldimethyidisiloxane | 0.00 | 0.07 |
| Finely divided Platinum metal | 0.00 | 0.01 |
| on Calcium Carbonate |  |  |
|  | 100.00 | 100.00 |

Example 4

A two component composition of the invention is made by first making a Base Paste and then a Catalyst Paste as described in Example 1, having the composition indicated in the table below.

|  | BASE | CATALYST |
|---|---|---|
| Organohydrogen Polysiloxane | 10.00 | 0.00 |
| (5000–7000 cps) QM resin dispersion | 19.40 | 32.37 |
| (45000–60000 cps) QM resin dispersion | 36.03 | 36.03 |
| Cristobalite | 20.00 | 20.00 |
| Diatomaceious earth | 5.00 | 5.00 |
| Cab-O-Sil TS-530 | 5.00 | 5.00 |
| Pigments Predispersed in Divinyl Polysiloxane | 1.50 | 0.00 |
| Titanium Oxide Pigment | 0.07 | 0.07 |
| Surfactant (Igepal CO-530) | 3.00 | 0.00 |
| Plasticizer | 0.00 | 0.50 |
| Platinum Catalyst | 0.00 | 1.00 |
| 1,3-Divinyldimethyidisiloxane | 0.00 | 0.03 |
| Finely divided Platinum metal | 0.00 | 0.00 |
| on Calcium Carbonate |  |  |
|  | 100.00 | 100.00 |

Example 5

A two component composition of the invention is made by first making a Base Paste and then a Catalyst Paste as described in Example 1, having the composition indicated in the table below.

|  | BASE | CATALYST |
|---|---|---|
| Organohydrogen Polysiloxane | 11.00 | 0.00 |
| (5000–7000 cps) QM resin dispersion | 14.36 | 28.44 |
| (45000–60000 cps) QM resin dispersion | 43.07 | 42.64 |
| Cristobalite | 17.00 | 17.19 |
| Diatomaceious earth | 5.00 | 4.95 |
| Cab-O-Sil TS-530 | 5.00 | 4.95 |
| Pigments Predispersed in Divinyl Polysiloxane | 1.50 | 0.00 |
| Titanium Oxide Pigment | 0.07 | 0.07 |
| Surfactant (Igepal CO-530) | 3.00 | 0.00 |
| Plasticizer | 0.00 | 0.49 |
| Platinum Catalyst | 0.00 | 1.13 |
| 1,3-Divinyldimethyidisiloxane | 0.00 | 0.06 |
| Finely divided Platinum metal | 0.00 | 0.09 |
| on Calcium Carbonate |  |  |
|  | 100.00 | 100.00 |

Example 6

A two component composition of the invention is made by first making a Base Paste and then a Catalyst Paste as described in Example 1, having the composition indicated in the table below.

|  | BASE | CATALYST |
|---|---|---|
| Organohydrogen Polysiloxane | 9.52 | 0.00 |
| (5000–7000 cps) QM resin dispersion | 11.19 | 27.91 |
| (45000–60000 cps) QM resin dispersion | 38.07 | 38.21 |
| Cristobalite | 22.84 | 21.21 |
| Diatomaceious earth | 5.71 | 5.73 |
| Cab-O-Sil TS-530 | 5.71 | 5.73 |
| Pigments Predispersed in Divinyl Polysiloxane | 1.58 | 0.00 |
| Titanium Oxide Pigment | 0.13 | 0.13 |
| Surfactant (Igepal CO-530) | 4.76 | 0.00 |
| Plasticizer | 0.48 | 0.48 |
| Platinum Catalyst | 0.00 | 0.48 |
| 1,3-Divinyldimethyidisiloxane | 0.00 | 0.05 |
| Finely divided Platinum metal | 0.00 | 0.08 |
| on Calcium Carbonate |  |  |
|  | 100.00 | 100.00 |

Example 7

A two component composition of the invention is made by first making a Base Paste and then a Catalyst Paste as described in Example 1, having the composition indicated in the table below.

|  | BASE | CATALYST |
|---|---|---|
| Organohydrogen Polysiloxane | 9.52 | 0.00 |
| (5000–7000 cps) QM resin dispersion | 11.19 | 27.91 |
| (45000–60000 cps) QM resin dispersion | 38.07 | 38.21 |
| Cristobalite | 22.84 | 21.21 |
| Diatomaceious earth | 5.71 | 5.73 |
| Cab-O-Sil TS-530 | 5.71 | 5.73 |
| Pigments Predispersed in Divinyl Polysiloxane | 1.58 | 0.00 |
| Titanium Oxide Pigment | 0.13 | 0.13 |
| Surfactant (Igepal CO-530) | 4.76 | 0.00 |
| Plasticizer | 0.48 | 0.48 |
| Platinum Catalyst | 0.00 | 0.48 |
| 1,3-Divinyldimethyidisiloxane | 0.00 | 0.05 |
| Finely divided Platinum metal | 0.00 | 0.08 |
| on Calcium Carbonate |  |  |
|  | 100.00 | 100.00 |

Example 8

A two component composition of the invention is made by first making a Base Paste and then a Catalyst Paste as described in Example 1, having the composition indicated in the table below.

|  | BASE | CATALYST |
|---|---|---|
| Organohydrogen Polysiloxane | 9.52 | 0.00 |
| (5000–7000 cps) QM resin dispersion | 11.19 | 27.91 |
| (45000–60000 cps) QM resin dispersion | 38.07 | 38.21 |
| Cristobalite | 22.84 | 21.21 |
| Diatomaceious earth | 5.71 | 5.73 |
| Cab-O-Sil TS-530 | 5.71 | 5.73 |
| Pigments Predispersed in Divinyl Polysiloxane | 1.58 | 0.00 |
| Titanium Oxide Pigment | 0.13 | 0.13 |
| Surfactant (Igepal CO-530) | 4.76 | 0.00 |
| Plasticizer | 0.48 | 0.48 |
| Platinum Catalyst | 0.00 | 0.48 |

-continued

|  | BASE | CATALYST |
|---|---|---|
| 1,3-Divinyldimethyidisiloxane | 0.00 | 0.05 |
| Finely divided Platinum metal | 0.00 | 0.08 |
| on Calcium Carbonate |  |  |
|  | 100.00 | 100.00 |

Example 9

A two component composition of the invention is made by first making a Base Paste and then a Catalyst Paste as described in Example 1, having the composition indicated in the table below.

|  | BASE | CATALYST |
|---|---|---|
| Organohydrogen Polysiloxane | 9.52 | 0.00 |
| (5000–7000 cps) QM resin dispersion | 11.19 | 27.91 |
| (45000–60000 cps) QM resin dispersion | 38.07 | 38.21 |
| Cristobalite | 22.84 | 21.21 |
| Diatomaceious earth | 5.71 | 5.73 |
| Cab-O-Sil TS-530 | 5.71 | 5.73 |
| Pigments Predispersed in Divinyl Polysiloxane | 1.58 | 0.00 |
| Titanium Oxide Pigment | 0.13 | 0.13 |
| Surfactant (Igepal CO-530) | 4.76 | 0.00 |
| Plasticizer | 0.48 | 0.48 |
| Platinum Catalyst | 0.00 | 0.48 |
| 1,3-Divinyldimethyidisiloxane | 0.00 | 0.05 |
| Finely divided Platinum metal | 0.00 | 0.08 |
| on Calcium Carbonate |  |  |
|  | 100.00 | 100.00 |

Example 10

A two component composition of the invention is made by first making a Base Paste and then a Catalyst Paste as described in Example 1, having the composition indicated in the table below.

|  | BASE | CATALYST |
|---|---|---|
| Organohydrogen Polysiloxane | 9.52 | 0.00 |
| (5000–7000 cps) QM resin dispersion | 11.19 | 27.91 |
| (45000–60000 cps) QM resin dispersion | 38.07 | 38.21 |
| Cristobalite | 22.84 | 21.21 |
| Diatomaceious earth | 5.71 | 5.73 |
| Cab-O-Sil TS-530 | 5.71 | 5.73 |
| Pigments Predispersed in Divinyl Polysiloxane | 1.58 | 0.00 |
| Titanium Oxide Pigment | 0.13 | 0.13 |
| Surfactant (Igepal CO-530) | 4.76 | 0.00 |
| Plasticizer | 0.48 | 0.48 |
| Platinum Catalyst | 0.00 | 0.48 |
| 1,3-Divinyldimethyidisiloxane | 0.00 | 0.05 |
| Finely divided Platinum metal | 0.00 | 0.08 |
| on Calcium Carbonate |  |  |
|  | 100.00 | 100.00 |

Example 11

A representative sample of each of the above described Examples, of 10 grams, is mixed in equal parts and the properties of the mixture and resulting polymerized composition tested. The table below reports the results said measurements. The first five properties reported are tested in accord with ADA Specification 19: Non-Aqueous Elastomer Impression Materials (1976, as amended in 19a of 1982).

The following procedure was used to provide tensile tear strength, percent elongation, and modulus of elasticity of the Examples.

Equal parts of the base and catalyst components are mixed and the samples or specimen is placed in a specimen mold having an I-shaped cavity that is 1.5 mm thick, 20 mm×11 mm, with top arms of 8 mm depth and center I portion 5 mm wide. The filled mold is clamped between two stainless steel plates and the assembly is placed in a 32° C. water bath. At six minutes from start of mix, the assembly is removed from the bath. The mold is unclamped, the specimen is removed from the mold and any flash is removed from the specimen. At 10 minutes from start of mix the specimen is clamped into the specimen test grips of an instron Model 1123 in the extension mode. The Instron is attached to a Microcon II micropressor that has been programmed to calculate the tear strength [psi],% elongation, and modulus of elasticity. At 11 minutes, the specimen is stressed by the Instron at a rate of 10 mm/min. until the specimen reaches peak failure. (The maximum load is set to 5 kg.) This is repeated for five specimens and then statistically evaluated results are reported, as shown in the Table.

Wetting contact angles are measured for each Example as follows. One gram (1 g) of base and one gram (1 g) of catalyst paste are mixed together until uniform (~30 seconds). A one-half gram (0.5 g) of mixed paste is placed between two sheets of polyethylene (Dentsilk) and pressed flat using a glass plate, about 2–3 mm thick. The specimen is allowed to stand undisturbed until set (~15 minutes). The polyethylene sheets are removed, being careful not to touch the surface of the specimen, and the specimen placed on the table of a gynometer, a well known device for measuring contact angles. The eyepiece recticle is adjusted to the horizontal and vertical planes of the specimen surface and stop watch is started as a drop of water is dropped onto the specimen surface. At 1.5 minutes to 3.5 minutes, the inside contact angle, in degrees, of the water/specimen interface is measured using the gynometer scale, recorded for the specimen and reported below.

TABLE

PROPERTIES OF EXAMPLES

| Property | \multicolumn{10}{c}{Examples} | | | | | | | | | |
|---|---|---|---|---|---|---|---|---|---|---|
| | 1 | 2 | 3 | 4 | 5 | 6 | 7 | 8 | 9 | 10 |
| Work Time (min) | 3 | 3 | 3 | 2 | 3 | 4.25 | 2.50 | 3.33 | 3.18 | 2.50 |
| Set Time (min) | 6 | 6 | 6 | 4 | 6 | 9 | 5 | 7 | 7 | 5.75 |
| % Deformation | 0.5 | 0.25 | 0.45 | 0.3 | 1.9 | 4.25 | 1.75 | 2.25 | 23 | 1.65 |
| % Strain | 2.75 | 3.15 | 3.25 | 2.75 | 3.5 | NA | NA | NA | NA | NA |
| Consistency (mm) | 33 | 34 | 36 | 32 | 38 | 33 | 29 | 32 | 31 | 30 |
| Contact Angle° with water at 3 min. | 30 | 35 | 38 | 37 | 42 | 28 | 52 | 56 | 42 | 31 |
| Tear Strength PSI | 277 | 277 | 295 | 289 | 216 | NA | NA | NA | NA | NA |

Examples 1–3 are preferred compositions. Example 1 is suitable for dispensing from a tube and hand mixing. Example 2 is most preferred for cartridge dispensing and static-mixing. Example 3 describes a composition of the invention that is suitable for forming a lower viscosity composition suitable for either tube or cartridge dispensing.

The composition of Example 4, having a high viscosity, exhibited severe gassing, having a higher hydride concentration and no degassing component. Example 5, having a low viscosity, demonstrated good syringe consistency but had a high percent deformation and percent strain while tear strength was lower. This composition had a high hydride, low surfactant, low retarder and low catalyst concentration. Compositions of Examples 6, 8 and 9 did not polymerize properly. The composition of Example 6 had too low retarder and catalyst. The surfactant was also too high an HLB and too acid. The composition of Example 7 lacked wetting capability having a surface contact angle exceeding desirable limits. Examples 8 and 9 both were too low in retarder and catalyst concentrations The composition of Example 10 exceeded desired percent deformation.

I claim:

1. A polymerizable polyorganosiloxane composition, including a catalyst for polymerization, said composition for making a dental impression, comprising:

(a) a QM resin, containing vinyl groups;

(b) a linear vinyl terminated polydimethyl-siloxane fluid, forming with said QM resin a dispersion having a vinyl content of about 0.16 to 0.24 m-mole/g;

(c) an organohydrogen polysiloxane for cross-linking said vinyl groups;

(d) an organoplatinum catalyst complex for accelerating polymerization of said components;

(e) an emulsifying plasticizer for said catalyst complex;

(f) a retarder component in sufficient amount for temporarily delaying the onset of said polymerization;

(g) a filler; and (h) a surfactant that imparts wettability to said composition, wherein said composition surface contact angle with water is less than 50° after three minutes wherein the OM resin-containing dispersion comprises: a first dispersion having a viscosity of about 5,000–7,000 cps: and a second dispersion having a viscosity of about 45,000–60,000 cps, said OM resin comprising about 20–25 weight % of said dispersions.

2. The composition of claim 1 wherein the dispersion of (a) and (b) has a viscosity of about 5,000–60,000 cps.

3. The composition of claim 1 wherein said QM resin comprises a polyorganosiloxane comprising units of $SiO_{4/2}$ and up to four units of $R^1R^2_2 SiO_{1/2}$ wherein $R^1$ is unsaturated hydrocarbon and
$R^2$ is alkyl or aryl.

4. The composition of claim 3, wherein said QM resin comprises the formula:

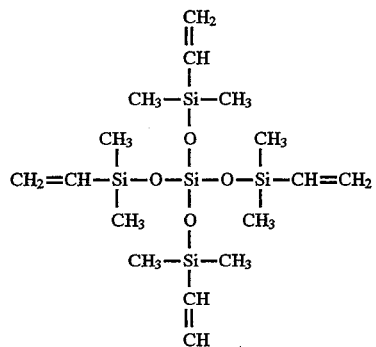

5. The composition of claim 1 further comprising a finely divided platinum metal, sufficient to scavenge excess hydrogen gas generated during polymerization of said composition.

6. The composition of claim 1 wherein said retarder component is a low molecular weight, vinyl functional fluid that is a linear or cyclic polysiloxane, in an amount of at least about 0.030 weight percent of said composition.

7. The composition of claim 6 wherein said retarder component comprises: a fluid 1,3-divinyl, dimethyldisiloxane, in an amount of about 0.030 to 0.10 weight percent of said composition.

8. The composition of claim 1 wherein said emulsifying plasticizer imparts handling and flow properties to said catalyst complex such that the composition is suitable for taking a dental impression.

9. The composition of claim 1 wherein said plasticizer is octyl benzyl phthalate.

10. The composition of claim 1 wherein said filler comprises about 15 to about 45 weight percent of said composition.

11. The composition of claim 10 wherein said filler comprises a mixture of about 14–24 weight percent crystalline silicone dioxide, about 3–6 weight percent amorphous silicone dioxide and about 4–8 weight percent silanated fumed silicone dioxide each based on 100% weight percent of the composition.

12. The composition of claim 11 wherein said filler comprises about 19% cristobalite at about 4–6µ particle diameter, about 6% diatomaceous earth at about 4–7µ particle diameter and about 4% silanated fumed silica at about 160–240 m²/g each based on 100% weight percent of the composition.

13. The composition of claim 1 wherein said surfactant comprises an HLB of about 8–11 and a pH of about 6–8.

14. The composition of claim 13 wherein said surfactant is a nonionic surfactant.

15. The composition of claim 14 wherein said surfactant is a nonylphenoxypoly (ethylenoxy) ethanol having an HLB of about 10.8.

16. The composition of claim 1 having, after polymerization, through chemical bonding, a tear strength of about 270–300 PSI and a contact angle with water of less than 50° at three minutes.

17. A method to taking a dental impression, in a wet environment, of oral hard and soft tissues, comprising:
   mixing a polymerizable polyorganosiloxane composition, including a polymerization catalyst comprising,
   (a) a QM resin, containing vinyl groups,
   (b) a linear vinyl terminated polydimethyl-siloxane fluid, forming with said QM resin a dispersion having a viscosity of about 5000–60,000 cps and a vinyl content of about 0.16 to 0.24 m-mole/g,
   (c) an organohydrogen polysiloxane having a viscosity of about 35–45 cps for cross-linking said vinyl groups,
   (d) an organoplatinum catalyst complex for accelerating polymerization of said components,
   (e) an emulsifying plasticizer for said catalyst complex component,
   (f) a retarder component in sufficient amount for temporarily delaying the onset of said polymerization,
   (g) a filler, and
   (h) a surfactant that imparts wettability to said composition, wherein said composition surface contact angle with water is less than 50° after three minutes;
   placing said mixture into contact with said tissues;
   allowing said mixture to harden into said impression; and
   removing said impression from said tissues;
   wherein the OM resin-containing dispersion, comprises a first dispersion having a viscosity of about 5,000–7,00Q cps; and a second dispersion having a viscosity of about 45,000–60,000 cps, said OM resin comprising about 20–25 weight % of said dispersions.

18. The method of claim 17 wherein said composition surface contact angle With water is less than about 50° from about two minutes from placing until said impression hardens.

19. A dental impression made by the method of claim 17.

20. The dental impression of claim 19 having a tear strength of at least about 270 PSI and a surface contact angle with water at three minutes of less than about 50°.

21. A method of making a two component polymerizable polyorganosiloxane composition, one component including a polymerization catalyst, comprising:
   (a) forming a first component, including,
      (i) a QM resin containing vinyl groups, dispersed in a linear vinyl terminated polydimethylsiloxane fluid, said dispersion having a viscosity of about 5,000–60,000 cps and a vinyl content of about 0.16 to 0.24 m-mole/g,
      (ii) an organohydrogen polysiloxane having a viscosity of about 35–45 cps for cross-linking said vinyl groups,
      (iii) a filler, and
      (iv) a surfactant that imparts wettability to said composition, wherein said composition surface contact angle with water is less than 50° after three minutes and wherein said OM resin-containing dispersion, comprises a first dispersion having a viscosity of about 5,000–7,000 cps; and a second dispersion having a viscosity of about 45,000–60,000 cps, said OM resin comprising about 20–25 weight % of said dispersions;
   (b) mixing a second component, comprising,
      (i) a QM resin containing vinyl groups, dispersed in a linear vinyl terminated polydimethylsiloxane fluid, said dispersion having a viscosity of about 5000–60,000 cps and a vinyl content of about 0.16 to 0.24 m-mole/g,
      (ii) a filler,
      (iii) an organoplatinum catalyst complex for accelerating polymerization of said components, and
      (iv) a retarder component in sufficient amount for temporarily delaying the onset of said polymerization; and
   (c) storing components (a) and (b) until ready for use.

22. The method of claim 21 said component (b) further including an emulsifying plasticizer for said catalyst component and hydrogen scavenging finely divided Pt metal.

23. A method of taking an impression of a dentition, comprising:
   (i) mixing components (a) and (b) of claim 21;
   (ii) placing said mixture into contact with said dentition;
   (iii) allowing said mixture to polymerize to dimensional stability; and (iv) removing said impression from said dentition.

24. A polymerizable polyorganosiloxane composition, including a catalyst for polymerization, said composition for making a dental impression, comprising:
   (a) a QM resin, containing vinyl groups;
   (b) a linear vinyl terminated polydimethyl-siloxane fluid, forming with said QM resin a dispersion having a vinyl content of about 0.16 to 0.24 m-mole/g;
   (c) an organohydrogen polysiloxane for cross-linking said vinyl groups;
   (d) an organoplatinum catalyst complex for accelerating polymerization of said components;
   (e) an emulsifying plasticizer for said catalyst complex;
   (f) a retarder component in sufficient amount for temporarily delaying the onset of said polymerization;
   (g) a filler, wherein said filler comprises about 15 to about 45 weight percent of said composition, and wherein herein said filler comprises a mixture of about 14–24 weight percent crystalline silicone dioxide, about 3–6 weight percent amorphous silicone dioxide and about 4–8 weight percent silanated fumed silicone dioxide each based on 100% weight percent of the composition; and
   (h) a surfactant that imparts wettability to said composition, wherein said composition surface contact angle with water is less than 50° after three minutes.

25. The composition of claim 24 wherein said filler comprises about 19% cristobalite at about 4–6μ particle diameter, about 6% diatomaceous earth at about 4–7μ particle diameter and about 4% silanated fumed silica at about 160–240 m²/g each based on 100% weight percent of the composition.

26. A method of making a polymerizable polyorganosiloxane composition, including a polymerization catalyst, comprising:
   (a) forming a first dispersion, including,
      (i) a QM resin containing vinyl groups, dispersed in a linear vinyl terminated polydimethylsiloxane fluid, said dispersion having a viscosity of about 5,000–60,000 cps and a vinyl content of about 0.16 to 0.24 m-mole/g, (ii) an organohydrogen polysiloxane having a viscosity of about 35–45 cps for cross-linking said vinyl groups, (iii) a filler wherein said filler comprises about 15 to about 45 weight percent of said composition, and wherein herein said filler comprises a mixture of about 14–24 weight percent crystalline silicone dioxide, about 3–6 weight percent amorphous silicone dioxide and about 4–8 weight percent silanated fumed silicone dioxide each based on 100% weight percent of the composition; and (iv) a surfactant that imparts wettability to said composition, wherein said composition surface contact angle with water is less than 50° after three minutes; and, (b) mixing a second dispersion, comprising, (i) a QM resin containing vinyl groups, dispersed in a linear vinyl terminated polydimethylsiloxane fluid, said dispersion having a viscosity of about 5000–60,000 cps and a vinyl content of about 0.16 to 0.24 m-mole/g, (ii) a filler, (iii) an organoplatinum catalyst complex for accelerating polymerization of said components, and (iv) a retarder component in sufficient amount for temporarily delaying the onset of said polymerization; and (c) storing dispersions (a) and (b) until ready for use.

* * * * *